United States Patent [19]

Johansen

[11] 3,943,917

[45] Mar. 16, 1976

[54] METHOD FOR COLLECTING BLOOD SAMPLES

[75] Inventor: Ebbe Johansen, Birkerod, Denmark

[73] Assignee: Radiometer A/S, Denmark

[22] Filed: May 12, 1975

[21] Appl. No.: 576,676

Related U.S. Application Data

[63] Continuation of Ser. No. 412,566, Nov. 5, 1973, abandoned.

[30] Foreign Application Priority Data

Nov. 6, 1972 Denmark .......................... 5492/72

[52] U.S. Cl. ........................... 128/2 F; 128/DIG. 5
[51] Int. Cl.² ............................................. A61B 5/00
[58] Field of Search ....... 128/2 F, DIG. 5, 276, 278, 128/218, 220

[56] References Cited
UNITED STATES PATENTS

| | | | |
|---|---|---|---|
| 1,272,742 | 7/1918 | Weguelin et al. ............... | 128/218 M |
| 1,526,595 | 2/1925 | Gillman .......................... | 128/DIG. 5 |
| 1,557,837 | 10/1925 | Hein ............................... | 128/218 R |
| 1,643,531 | 9/1927 | Wolf ................................ | 128/220 |
| 1,881,415 | 10/1932 | Tingleff .......................... | 128/DIG. 5 |
| 2,111,985 | 3/1938 | Meyer ............................. | 310/6 X |
| 3,016,896 | 1/1962 | Van Sickle ...................... | 128/218 P |
| 3,076,456 | 2/1963 | Hunt, Sr. ......................... | 128/218 M |
| 3,433,216 | 3/1969 | Mattson .......................... | 128/DIG. 5 |
| 3,623,475 | 11/1971 | Sanz et al. ...................... | 128/DIG. 5 |

FOREIGN PATENTS OR APPLICATIONS

116,726 6/1918 United Kingdom ............. 128/218 R

*Primary Examiner*—John D. Yasko
*Attorney, Agent, or Firm*—Robert E. Burns; Emmanuel J. Lobato; Bruce L. Adams

[57] ABSTRACT

The invention relates to a method for collecting a blood sample from a blood vessel, such as an artery, by means of a syringe, preferably of the type having a piston displaceably mounted within a cylinder which is provided with a hollow needle. Before the needle is inserted in the blood vessel from which the blood sample is to be collected the piston is displaced to a retracted position, and the cylinder space defined by the piston is vented to the atmosphere. The invention also relates to a blood sampling syringe having means for venting the cylinder space to the atmosphere in a retracted position of the syringe piston.

2 Claims, 9 Drawing Figures

METHOD FOR COLLECTING BLOOD SAMPLES

This is a continuation, of application Ser. No. 412,566, filed Nov. 5, 1973 now abandoned.

BACKGROUND OF THE INVENTION

1. Field of the Invention

The present invention relates to a method and an apparatus or a syringe for collecting a blood sample from a human or animal blood vessel, such as an artery or vein.

2. Description of the Prior Art

Arteries are blood vessels through which blood is passed from the lungs to the tissues in human or animal bodies, and the blood is passed from the tissues back to the lungs through the veins. Therefore, artery blood contains oxygen being used for combustion or oxidation processes in the tissues, and the blood in the veins transports carbon dioxide generated in the oxidation processes back to the lungs. The object of certain blood examinations — the so-called acid-base tests — is i.e., to establish a value indicating the lung effectively or the oxygen contents of the artery blood.

Several methods for collecting blood samples to be used for the said tests are known. Thus, it is known to collect a blood sample from an artery by means of a syringe of the type having a cylinder provided with a hollow needle or hypodermic needle and a piston displaceably mounted in the cylinder. According to the said known method the main artery in the upper arm (arteria brachialis), in the wrist (arteria radialis), or in the thigh (arteria femoralis) is punctured by means of the syringe needle while the piston is in its advanced position, and thereafter a suitable blood sample is sucked into the syringe cylinder by retracting the piston. However, the arteries are rather deep-lying and not easily accessible, and therefore it may be rather difficult to hit the artery with the syringe needle and it cannot be ascertained whether the artery has been properly punctured by the needle before the piston of the syringe is being retracted in relation to the cylinder. In case no proper puncturing has taken place a new attept must be made to hit the artery. Furthermore, it is difficult to keep the syringe needle completely still after its puncture of the artery, partly because the position of the hands holding the syringe have to be changed, and partly due to the friction between the piston and the syringe cylinder. Therefore, during retraction of the piston the needle point may be moved to such an extent that it slips out of the artery and/or increases the size of the hole made in the artery wall. Due to these facts collection of blood samples from arteries by the known method described is painful as well as subject to risk, and therefore in a number of countries such collection of blood samples is allowed to be made by doctors only.

In order to avoid the painful and risky artery puncture to the farthest possible extent it is sometimes replaced by the so-called capillary tube technique involving local increase of blood circulation in a tissue (for example in a heel, an ear, or a finger tip) by massage, the action of heat, or in another manner, whereby the oxygen content of the blood in the said tissue is increased so that that the blood becomes similar to artery blood. In accordance with said capillary tube technique a blood sample is collected by making a small incision in the said tissue in order to create a small drop of blood which is sucked into a capillary tube by inserting one end thereof into a drop of blood. By making the previously mentioned tests of blood samples collected by the capillary tube technique it is possible to obtain an acceptable accuracy compared with corresponding measurements made on real artery blood, but naturally by using the capillary tube technique it is possible to collect only relatively small blood samples which are insufficient to be treated in modern fully automatic or semi-automatic blood analyzing apparatuses. Furthermore, it is not possible to use the capillary tube technique in collecting blood samples from patients suffering from shock, because the blood vessels in the tissues are constricted in such a shock condition.

It is also known to avoid the problems in connection with artery puncture by making the measurements desired on vein blood instead of on artery blood and thereafter on the basis of empirically determined normal values try to compensate for the errors appearing in the measuring results due to the use of the vein blood instead of artery blood. The lastmentioned method has the advantage that the blood sample collecting technique for vein blood is relatively simple, without risk, and substantially without pain, but the results obtained by the measurements are of course rather inaccurate.

SUMMARY OF THE INVENTION

According to the invention a method has been provided for collecting a blood sample from a human or animal blood vessel by means of a syringe which comprises a hollow needle and a syringe chamber communicating with one end of the bore in said hollow needle and having a volume variable between a first volume and a second, substantially reduced volume, said method comprising puncturing said blood vessel by the free end of said hollow needle while said syringe chamber attains its said first volume and while the syringe chamber is vented to the atmosphere. In blood vessels the blood pressure is higher than the atmospheric pressure and therefore blood will start flowing into the vented syringe chamber as soon as the blood vessel has been properly punctured by the needle point, and provided that at least part of the walls of the syringe chamber is made from a transparent material it is possible to see when blood flows into the syringe chamber, and thereby it may be ascertained whether the blood vessel has been punctured or not. When using the method according to the invention the syringe may rather easily be kept still because no piston has to be retracted in order to suck blood from the blood vessel as is the case in the known method described above. Thus, the method according to the invention makes it possible to collect blood samples from arteries with substantially less pain or inconvenience for the patient than when the described known method for collecting blood samples from arteries is used. Although the advantages of the method according to the invention have special relation to collection of blood samples from arteries the method according to the invention may also advantageously be used in connection with collection of blood samples from veins, especially when these samples later should be injected and analyzed in automatic or semi-automatic blood analyzing apparatuses.

Because it is normally of interest to measure i.a. the partial pressures of oxygen and carbon dioxide in the blood sample collected it is important to avoid that the blood sample is in contact with atmospheric air for an extended period of time, because gases dissolved in the blood samples would then diffuse out into the atmospheric air. According to the invention this may be avoided by blocking the communication between the syringe chamber and the ambient atmosphere as soon as a sufficient amount of blood has been collected in the syringe chamber. If desired, the air remaining within the syringe chamber may thereafter be expelled through the hollow needle in a manner known per se. It has been found that the contact between the atmospheric air and the free surface of the blood sample during collection of the same does not affect the results of the later measurements.

The syringe used in the method according to the invention may be of any suitable type. Thus, for example, the syringe chamber may be compressible so that the said first volume corresponds to an uncompressed condition of the syringe chamber whereas the said second, substantially reduced volume corresponds to a compressed condition of the syringe chamber. The syringe used is, however, preferably of the type having a cylinder and a piston arranged displaceably therein, and in that case the said first volume corresponds to a retracted position of the piston, whereas the said second volume corresponds to an advanced position of the piston.

The invention also relates to a blood sampling syringe for collecting a blood sample from a human or animal blood vessel, said syringe comprises a hollow needle, a syringe chamber communicating with one end of the bore in said needle and having a volume variable between a first volume and a second, substantially reduced volume, and means for venting said first volume of the syringe chamber to the atmosphere. The said syringe is preferably of the type having a cylinder and a piston displaceably arranged therein, and the cylinder wall is preferably partly or totally made from a transparent material, such as transparent plastic material. The syringe according to the invention may preferably be packed in sterile condition with the piston in its retracted position and with the inner cylinder chamber vented to the ambient atmosphere within the packing. The syringe is then ready for use as soon as it is removed from the packing. The syringe is preferably of the disposable type and made substantially from plastic material. It is not possible to use syringes made from plastic material in connection with the known method for collecting blood samples from arteries because of the relatively high friction between the piston and the inner cylinder wall. That friction is, however, of no importance in connection with the method according to the invention which does not involve displacement of the piston during collection of a blood sample.

BRIEF DESCRIPTION OF THE DRAWINGS

The invention will now be further described with reference to the drawings showing various embodiments of syringes according to the invention, and wherein.

DESCRIPTION OF THE PREFERRED EMBODIMENTS

Figure 1:
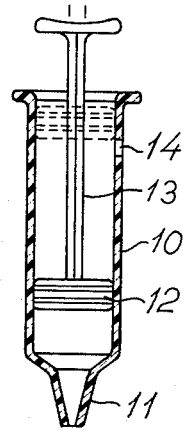
FIG. 1 is an elevational and partly sectional view of a first embodiment of the syringe according to the invention provided with an opening in the cylinder wall.

All of the syringes shown on the drawing comprises a syringe cylinder 10 having at one end a projection 11 with an outer surface formed substantially as a truncated cone and adapted to engage with a normal mounting member of a hollow needle or a hypodermic needle 11-(FIG. 8) in a known manner. A piston 12 having a piston rod 13 is displaceably mounted within the cylinder 10 which is preferably made of a transparent plastic material. The syringes shown are preferably of the disposable type.

Each of the syringes is provided with some kind of means making it possible to vent the cylinder space defined by the piston 12 in a retracted position thereof to the ambient atmosphere. In the embodiment shown in FIG. 1 the said venting means comprise an opening or hole 14 in the cylinder 10. When the syringe shown in FIG. 1 is to be used for collecting a blood sample from an artery or vein it is provided with a suitable hypodermic needle and the piston 12 is moved to its retracted position indicated by dotted lines if the piston is not already in that position. The cylinder space defined by the piston is now communicating with the atmosphere through the opening 14. The tip 11" of the syringe needle, which may preferably be a so-called tuberculine needle, may now be introduced into an artery or a vein, and when the blood vessel has been punctured by the needle point 11" blood will start flowing into the cylinder 10 due to the fact that the pressure within the blood vessel is above that of the atmosphere and that air may escape through the opening 14 from the cylinder space defined by the piston 12. When a suitable amount of blood has flowed into the cylinder 10 the needle is retracted from the blood vessel and the communication between the cylinder space and the ambient atmosphere may now be disrupted by displacing the piston 12 inwardly past the opening 14. Air which might be present within the cylinder space may simultaneously be expelled through the bore of the needle. The collected blood sample may be stored in the syringe until use and may then for example be injected directly into an automatically or semi-automatically functioning blood analyzer.

Figure 2:
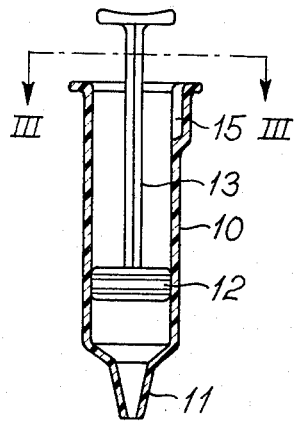
FIG. 2 is a similar view of a second embodiment having a longitudinally extending groove formed in the inner wall of the cylinder at one end thereof.
Figure 4:
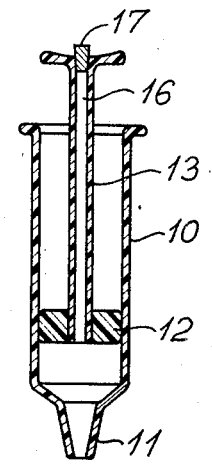
FIG. 4 is a sectional view of a third embodiment of the syringe according to the invention having a piston rod with an axially extending through bore or passage.
Figure 3:
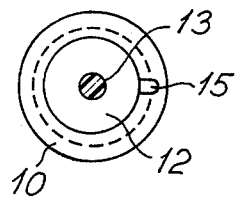
FIG. 3 is a cross-section viewd in the direction indicated by the arrows III — III in FIG. 2.

In the embodiment shown in FIGS. 2 and 3 the opening 14 is replaced by a longitudinally extending groove 15 which is formed in the inner wall of the cylinder 10 and communicates the cylinder space defined by the piston with the ambient atmosphere when the piston is positioned in its retracted position. In the embodiment shown in FIG. 4 the communication between the cylinder space defined by the piston 12 and the atmosphere is obtained by means of a through passage or bore which extends axially through the piston rod 13 and may be closed by means of a stopper 17 or another closure member. When the embodiment according to FIG. 4 is to be used for collecting a blood sample the stopper 17 is removed and the piston 12 is moved to its retracted position (if not already in that position) before puncturing of the blood vessel by means of the needle. When a blood sample has been collected the passage 16 may again be closed by means of the stopper 17.

Figure 6:
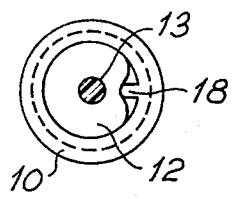
FIG. 6 is a cross-sectional view in the direction indicated by the arrows VI — VI in FIG. 5.
Figure 5:
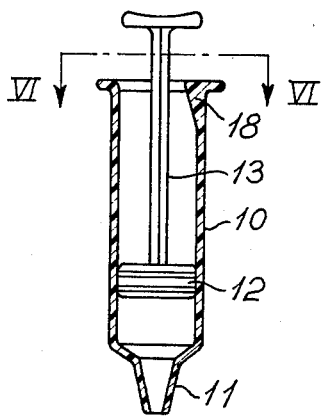
FIG. 5 is an elevational and partially sectional view of a fourth embodiment of the syringe according to the invention having a longitudinally extending ridge formed on the inner wall of the cylinder at one end thereof.

The embodiment shown in FIG. 5 comprises a wedge-shaped ridge 18 formed on the inner wall of the cylinder 10 at one end thereof, and as shown in FIG. 6 the said ridge provides a leak between the piston 12 and the surrounding cylinder wall when the piston is in its fully retracted position. The said leak establishes the necessary communication between the inner cylinder space and the ambient atmosphere during the collection of a blood sample.

Figure 9:
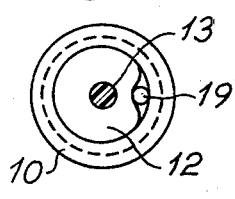
FIG. 9 is a cross-section viewed in direction of the arrows IX — IX in FIG. 8.
Figure 7:
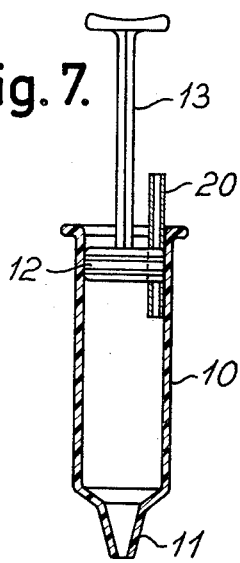
FIG. 7 is an elevational and partially sectional view in a fifth embodiment of the syringe according to the invention having a longitudinally extending venting tube arranged between the inner wall of the cylinder and the cylindrical surface of the piston.
Figure 8:
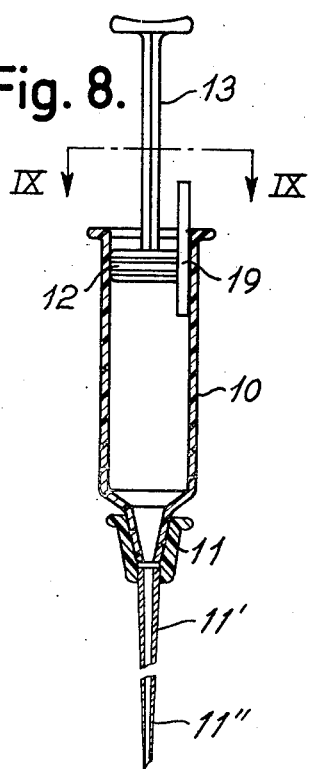
FIG. 8 is an elevational and partially sectional view of a sixth embodiment and having a longitudinally extending rod-shaped member arranged between the inner wall of the cylinder and the cylindrical surface of the piston.

A similar leak between the piston and the surrounding cylinder wall in the fully retracted position of the piston may be obtained by means of the embodiment shown in FIGS. 8 and 9 having a separate, rod-shaped member arranged between the inner wall of the cylinder 10 and the piston 12 in the retracted position thereof. In the embodiment shown in FIG. 7 the venting means comprises a corresponding tube-shaped member 20 which may be a section of a cannula forming a venting tube. When blood samples have been collected by means of the syringes shown in FIGS. 7 and 8 the communication between the cylinder space defined by the piston and the ambient atmosphere may be disrupted by removal of the rod-shaped member 19 and the tube section 20, respectively.

The syringe embodiments shown in FIGS. 7 and 8 — and possible also other embodiments of the syringe according to the invention — may preferably be packed in a sterile packing with the piston 12 in its fully retracted position and with or without a hollow needle mounted on the projection 11. In case the syringe is packed with the needle 11' mounted thereon the packing contains a sterile syringe ready for use in collecting a blood sample.

It should be understood that the embodiments shown on the drawing and described above are examples only and that various modifications and changes may be made within the scope of the appended claims.

I claim:

1. A method of collecting a blood sample for analyzing it, comprising;
   providing a syringe chamber with a first end normally communicating with the atmosphere and with a hollow needle communicating with and extending from an opposite end of the chamber to a free end of the needle;
   puncturing a blood vessel of a patient with the free end of the hollow needle;
   thereupon holding the syringe chamber immobile relative to the patient to quiescently pass a stream of blood from the punctured blood vessel through the hollow needle, by body pressure of the patient into the chamber, until a blood sample of predetermined volume has been collected in the chamber;
   then withdrawing the free end of the hollow needle from the blood vessel and terminating said holding of the syringe chamber; and
   thereafter interrupting the communication of the first end of the syringe chamber with the atmosphere and reducing the volume of the chamber to forcibly expel blood therefrom for analyzing the blood.

2. A method according to claim 1, wherein said blood vessel is an artery.

* * * * *